(12) United States Patent
Azhari et al.

(10) Patent No.: US 7,828,734 B2
(45) Date of Patent: *Nov. 9, 2010

(54) DEVICE FOR ULTRASOUND MONITORED TISSUE TREATMENT

(75) Inventors: Haim Azhari, Doar-Na Misgav (IL); Jacob Benarie, Haifa (IL); Yossi Gross, Moshav Mazor (IL); Liat Tsoref, Tel Aviv (IL)

(73) Assignee: Slender Medical Ltd., Herzliya (IL)

( * ) Notice: Subject to any disclaimer, the term of this patent is extended or adjusted under 35 U.S.C. 154(b) by 513 days.

This patent is subject to a terminal disclaimer.

(21) Appl. No.: 11/651,198

(22) Filed: Jan. 8, 2007

(65) Prior Publication Data

US 2008/0058682 A1 Mar. 6, 2008

Related U.S. Application Data

(60) Provisional application No. 60/809,577, filed on May 30, 2006, provisional application No. 60/780,772, filed on Mar. 9, 2006, provisional application No. 60/860,635, filed on Nov. 22, 2006.

(51) Int. Cl.
*A61B 8/00* (2006.01)
(52) U.S. Cl. ............... 600/439; 600/437; 601/2; 601/3; 310/311; 606/27; 606/32; 606/33; 606/34; 606/41
(58) Field of Classification Search ........... 600/437, 600/439; 601/2, 3; 310/311; 606/27, 32–34, 606/41
See application file for complete search history.

(56) References Cited

U.S. PATENT DOCUMENTS

| 4,792,788 | A | 12/1988 | Kumar |
|---|---|---|---|
| 5,143,063 | A | 9/1992 | Fellner |
| 5,143,073 | A | 9/1992 | Dory |
| 5,175,709 | A | 12/1992 | Slayton |
| 5,269,297 | A | 12/1993 | Weng |
| 5,601,526 | A | 2/1997 | Chapelon et al. |
| 5,618,275 | A * | 4/1997 | Bock .................. 604/290 |
| 5,620,479 | A | 4/1997 | Diederich |
| 5,671,747 | A | 9/1997 | Connor |
| 5,997,478 | A | 12/1999 | Jackson et al. |
| 6,071,239 | A | 6/2000 | Cribbs et al. |
| 6,113,558 | A | 9/2000 | Rosenschein et al. |
| 6,128,523 | A | 10/2000 | Bechtold et al. |
| 6,221,019 | B1 | 4/2001 | Kantrovich |

(Continued)

FOREIGN PATENT DOCUMENTS

WO WO 00/53263 9/2000

(Continued)

OTHER PUBLICATIONS

U.S. Provisional Patent U.S. Appl. No. 60/809,577.

(Continued)

*Primary Examiner*—Brian Casler
*Assistant Examiner*—James Kish
(74) *Attorney, Agent, or Firm*—Abelman, Frayne & Schwab

(57) ABSTRACT

Apparatus is provided, including a housing, adapted for placement on tissue of a subject, and a plurality of transducers, disposed at respective locations with respect to the housing, and configured to transmit energy towards each other, in a plane defined by the housing.

19 Claims, 2 Drawing Sheets

U.S. PATENT DOCUMENTS

| | | | |
|---|---|---|---|
| 6,350,276 B1 | 2/2002 | Knowlton | |
| 6,443,901 B1 | 9/2002 | Fraser | |
| 6,450,979 B1 | 9/2002 | Miwa et al. | |
| 6,470,216 B1 | 10/2002 | Knowlton | |
| 6,500,141 B1 | 12/2002 | Irion et al. | |
| 6,524,250 B1 * | 2/2003 | Weber et al. | 600/439 |
| 6,577,042 B2 | 6/2003 | Lee | |
| 6,599,256 B1 | 7/2003 | Acker et al. | |
| 6,607,498 B2 | 8/2003 | Eshel | |
| 6,626,854 B2 | 9/2003 | Freidman et al. | |
| 6,645,162 B2 | 11/2003 | Freidman et al. | |
| 6,730,034 B1 | 5/2004 | Lang et al. | |
| 6,860,852 B2 | 3/2005 | Schnenberger | |
| 6,971,994 B1 | 12/2005 | Young et al. | |
| 7,110,825 B2 | 9/2006 | Vaynberg | |
| 7,112,173 B1 | 9/2006 | Kantrovich | |
| 7,258,674 B2 | 8/2007 | Cribbs | |
| 7,273,459 B2 | 9/2007 | Desilets | |
| 7,282,047 B2 | 10/2007 | Zimmerman | |
| 7,311,679 B2 | 12/2007 | Desilets | |
| 7,331,951 B2 | 2/2008 | Eshel | |
| 7,347,855 B2 | 3/2008 | Eshel | |
| 7,399,284 B2 | 7/2008 | Miwa | |
| 7,473,224 B2 | 1/2009 | Makin | |
| 7,533,571 B2 | 5/2009 | Ariav et al. | |
| 7,559,905 B2 | 7/2009 | Kagosaki | |
| 2002/0082589 A1 | 6/2002 | Friedman et al. | |
| 2002/0193831 A1 | 12/2002 | Smith | |
| 2003/0065264 A1 | 4/2003 | Tsoref | |
| 2003/0083536 A1 | 5/2003 | Eshel et al. | |
| 2003/0171701 A1 | 9/2003 | Babaev | |
| 2004/0039312 A1 | 2/2004 | Hillstead et al. | |
| 2004/0215110 A1 | 10/2004 | Kreindel | |
| 2004/0217675 A1 | 11/2004 | Desilets et al. | |
| 2004/0254470 A1 | 12/2004 | Drinkwater et al. | |
| 2005/0049543 A1 | 3/2005 | Anderson et al. | |
| 2005/0154295 A1 | 7/2005 | Quistgaard et al. | |
| 2005/0154308 A1 | 7/2005 | Quistgaard et al. | |
| 2005/0154309 A1 | 7/2005 | Etchells et al. | |
| 2005/0154313 A1 | 7/2005 | Desilets et al. | |
| 2005/0154314 A1 | 7/2005 | Quistgaard et al. | |
| 2005/0154431 A1 | 7/2005 | Quistgaard et al. | |
| 2005/0187463 A1 | 8/2005 | Quistgaard et al. | |
| 2005/0187495 A1 | 8/2005 | Quistgaard et al. | |
| 2005/0193451 A1 | 9/2005 | Quistgaard et al. | |
| 2005/0245829 A1 | 11/2005 | Wakabayashi | |
| 2005/0261584 A1 | 11/2005 | Eshel et al. | |
| 2006/0036300 A1 | 2/2006 | Kreindel | |
| 2006/0047281 A1 | 3/2006 | Kreindel | |
| 2006/0094988 A1 | 5/2006 | Tosaya et al. | |
| 2006/0122509 A1 | 6/2006 | Desilets et al. | |
| 2006/0184024 A1 | 8/2006 | De Silva et al. | |
| 2006/0189976 A1 | 8/2006 | Karni | |
| 2006/0211958 A1 | 9/2006 | Rosenberg | |
| 2008/0076958 A1 | 3/2008 | Britva | |
| 2008/0183167 A1 | 7/2008 | Britva | |
| 2008/0234609 A1 | 9/2008 | Kreindel | |
| 2009/0012585 A1 | 1/2009 | Karni | |
| 2009/0076420 A1 | 3/2009 | Kreindel | |
| 2009/0171424 A1 | 7/2009 | Britva | |
| 2009/0221938 A1 | 9/2009 | Rosenberg | |
| 2009/0254068 A1 | 10/2009 | Karni | |

FOREIGN PATENT DOCUMENTS

| | | |
|---|---|---|
| WO | WO 2005/074365 | 8/2005 |
| WO | WO 2005/112807 | 12/2005 |
| WO | WO 2005/112815 | 12/2005 |
| WO | WO 2006/018837 | 2/2006 |
| WO | WO 2006/122136 | 11/2006 |
| WO | WO 2007/009118 | 1/2007 |
| WO | WO 2008/123951 | 10/2008 |

OTHER PUBLICATIONS

U.S. Provisional Patent U.S. Appl. No. 60/780,772.
U.S. Appl. No. 60/860,635.
Moran CM et al., "Ultrasonic propagation properties of excised human skin", Ultrasound Med Biol. 21(9):1177-90, 1995.
Akashi N et al., "Acoustic properties of selected bovine tissue in the frequency range 20-200MHz", J Acoust Soc Am. 98(6):3035-9, 1995.
An Office Action dated Jun. 10, 2009, which issued during the prosecution of Applicant's U.S. Appl. No. 11/653,115.
Office Action dated Mar. 17, 2010 received in U.S. Appl. No. 11/653,115.
Applicant's response dated May 17, 2010 to the Office Action of Mar. 17, 2010 in U.S. Appl. No. 11/653,115.
Correspondence from the USPTO dated Apr. 30, 2010 enclosing Interview Summary in U.S. Appl. No. 11/653,115.
Office Action dated Jun. 23, 2010 received in U.S. Appl. No. 11/653,115.
Applicants' response dated Jul. 19, 2010 to the Office Action dated Jun. 23, 2010 in U.S. Appl. No. 11/653,115.
Interview Summary in U.S. Appl. No. 11/653,115 dated Jul. 28, 2010.
A Statement of the Substance of the Interview dated Aug. 3, 2010 in U.S. Appl. No. 11/653,115.

* cited by examiner

DEVICE FOR ULTRASOUND MONITORED TISSUE TREATMENT

CROSS-REFERENCES TO RELATED APPLICATIONS

The present application claims the priority of:

U.S. Provisional Patent Application 60/809,577 to Azhari et al., filed May 30, 2006, entitled, "A device for ultrasound monitored tissue treatment,"

U.S. Provisional Patent Application 60/780,772 to Azhari et al., filed Mar. 9, 2006, entitled, "A method and system for lypolysis and body contouring," and U.S. Provisional Patent Application 60/860,635 to Azhari et al., filed Nov. 22, 2006, entitled, "Cosmetic tissue treatment using ultrasound."

Each of the above applications is incorporated herein by reference.

FIELD OF THE INVENTION

The present invention relates in general to tissue treatment by application of energy thereto, and specifically to the monitoring and applying of ultrasound to skin.

BACKGROUND OF THE INVENTION

Systems for applying energy to biological tissue are well known. Such energy application may be intended to heal injured tissue, ablate tissue, or improve the appearance of tissue. Energy may be applied in different forms, such as radiofrequency, laser, or ultrasound.

US Patent Application Publication 2004/0039312 to Hillstead et al., which is incorporated herein by reference, describes a system for the destruction of adipose tissue utilizing high intensity focused ultrasound (HIFU) within a patient's body. The system is described as comprising a controller for data storage and the operation and control of a plurality of elements. One element is described as a means for mapping a human body to establish three dimensional coordinate position data for existing adipose tissue. The controller is able to identify the plurality of adipose tissue locations on said human body and establish a protocol for the destruction of the adipose tissue. A HIFU transducer assembly having one or more piezoelectric element(s) is used along with at least one sensor, wherein the sensor provides feedback information to the controller for the safe operation of the piezoelectric element(s). The sensor is electronically coupled to the controller, and the controller provides essential treatment command information to one or more piezoelectric element (s) based on positioning information obtained from the three dimensional coordinate position data.

U.S. Pat. No. 6,500,141 to Irion et al., which is incorporated herein by reference, describes an apparatus for treating body tissue, in particular superficial soft tissue, with ultrasound, comprising an ultrasonic generation unit and an applicator, by means of which the ultrasound can be irradiated from an applicator surface facing the body surface from outside through the body surface into the body tissue. A suction apparatus for sucking in the body surface against the applicator surface is provided. An apparatus for treating body tissue including superficial soft tissue, with ultrasound, is described as comprising an ultrasonic generation unit and an applicator having an applicator surface facing the body surface from which the ultrasound can be irradiated through the body surface into the body tissue. A suction apparatus is provided for taking in the body surface against the applicator surface which is curved inwardly.

U.S. Pat. No. 5,601,526 to Chapelon et al., which is incorporated herein by reference, describes a method and apparatus for performing therapy using ultrasound. The apparatus is described as using a treatment device having at least one piezoelectric transducer element to supply ultrasonic waves focused onto a focal point or region that determines the tissue zone submitted to therapy. The treatment device, which is controlled by a control device, supplies two types of ultrasonic waves, the first one being thermal waves that produce a predominantly thermal effect on the tissue being treated and the second one being cavitation waves that produce a predominantly cavitation effect on the tissue to be treated. A therapy method is described, using ultrasound for the purpose of destroying a target. The target includes tissue, which may be located inside a body of a mammal. Ultrasonic waves are focused onto a focal point or region. A tissue zone to be submitted to the therapy is determined. Ultrasonic waves are supplied to the target. The ultrasonic waves of two types: thermal waves, for producing a predominantly thermal effect on tissue to be treated, and cavitation waves, for producing a predominantly cavitation effect on the tissue to be treated. The two types of waves are applied for a time sufficient to effect therapy by destroying at least a portion of the tissue, and the thermal ultrasonic waves are supplied at least at a beginning of treatment. In an embodiment, the ultrasonic waves are supplied after an adjustable predetermined time interval for allowing preheating of the tissue to be treated.

PCT Publication WO 06/018837 to Azhari et al., which is incorporated herein by reference, describes a method of damaging a target tissue of a subject. The method is described as comprising: (a) imaging a region containing the target tissue; (b) determining a focal region of a damaging radiation; (c) positioning the focal region onto the target tissue; and (d) damaging the target tissue by an effective amount of the damaging radiation. The determination of the focal region is described by delivering to the region bursts of ultrasonic radiation from a plurality of directions and at a plurality of different frequencies, and passively scanning the region so as to receive from the region ultrasonic radiation having at least one frequency other than the plurality of different frequencies.

US Patent Application Publications 2005/0154308, 2005/0154309, 2005/0193451, 2004/0217675, 2005/0154295, 2005/0154313, 2005/0154314, 2005/0154431, 2005/0187463, 2005/0187495, 2006/0122509, 2003/0083536, 2005/0261584, 2004/0215110, 2006/0036300, 2002/0193831, and 2006/0094988, U.S. Pat. Nos. 5,143,063, 6,730,034, 6,450,979, 6,113,558, 6,607,498, 6,626,854, 6,645,162, and 6,971,994, and PCT Patent Publications WO/2000/053263, and WO/2005/074365 are incorporated herein by reference.

SUMMARY OF THE INVENTION

In some embodiments of the invention, cosmetic and/or medical apparatus is provided which comprises a tissue monitoring system and a tissue treatment system. The monitoring system assesses a state of tissue of a subject, and the treatment system applies a treatment to the tissue. Typically, the monitoring and treatment occur in alternation, until the monitoring system determines that the treatment has been completed. For some applications, one of the systems comprises a housing, and the tissue of the subject is sucked at least partially into the housing, to allow the system to monitor or treat (as appropriate) the tissue that has been sucked into the housing. In this case, the system typically transmits ultrasound energy that is designated to remain in large part within the housing and tissue therein, and generally not to affect tissue outside of the housing.

As appropriate for a given application, the system comprising the housing may be the monitoring system, the treatment system, or both the monitoring system and the treatment system.

In an embodiment, the housing comprises a plurality of ultrasound transducers, arranged in a circle (or other typically but not necessarily closed shape). The transducers are positioned such that ultrasound energy transmitted by the transducers remains generally within a plane defined by the circle. Similarly, in embodiments in which the monitoring system comprises the housing, the transducers are typically disposed such that they are optimized to receive ultrasound energy coming generally from within the plane.

Treatments using the treatment system may include, as appropriate, causing heating, tissue damage, thermal ablation, mechanical irritation, cell structure alteration, augmented diffusion, and/or a cavitation effect.

Typically, the treatment system comprises circuitry for configuring the applied energy as high intensity focused ultrasound (HIFU), using techniques known in the art.

For some applications, the housing is flexible, e.g., to allow the treatment of limbs or other curved body parts. Alternatively, the housing is generally rigid.

In an embodiment, the monitoring system generally continuously generates acoustic maps or images, depicting changes occurring during a treatment of the tissue within the housing. For some applications, this allows an operator of the treatment system to monitor the progress of a treatment, and to alter a parameter of the treatment in response thereto. Such a parameter may include, for example, a location of a focus of the HIFU, a positioning of the housing on the subject's skin, or a strength of the applied energy. Alternatively or additionally, the treatment system and monitoring system operate in a closed loop fashion, whereby an output of the monitoring system (e.g., a location of fatty tissue) is used as an input parameter to the treatment system, such that the treatment system can adjust its operating parameters in response to the output of the monitoring system (and, for example, heat the fatty tissue).

There is therefore provided, in accordance with an embodiment of the invention, apparatus, including:

a housing, adapted for placement on tissue of a subject; and a plurality of transducers, disposed at respective locations with respect to the housing, and configured to transmit energy towards each other, in a plane defined by the housing.

In an embodiment, the plurality of transducers are disposed with respect to the housing so as to define a ring of transducers.

In an embodiment, the apparatus includes a source of suction configured to draw the tissue into the housing, and the transducers are disposed with respect to the housing so as to direct the energy into the tissue within the housing.

In an embodiment, the apparatus includes a pinching tool, configured to draw the tissue into the housing by pinching the tissue, and the transducers are disposed with respect to the housing so as to direct the energy into the tissue within the housing.

In an embodiment, the transducers are configured to substantially avoid transmitting energy out of the plane.

In an embodiment, the transducers include ultrasound transducers.

In an embodiment, the tissue includes skin of the subject, and wherein the transducers are configured to transmit the energy through the skin.

In an embodiment, the housing is flexible at least in part, and configured to flex to match a shape of the tissue.

In an embodiment, the housing is generally rigid.

In an embodiment, the apparatus is configured to apply a treatment to the tissue without monitoring a state of the tissue.

In an embodiment, the apparatus is configured to apply a treatment to the tissue by elevating a temperature of the tissue by less than 10 C. In an embodiment, the apparatus is configured to elevate the temperature by less than 5 C.

In an embodiment, the apparatus is configured to receive energy in response to the transmitted energy, and to monitor a state of the tissue in response to the received energy.

In an embodiment, the plurality of transducers are configured to cycle repeatedly between (a) applying a treatment to the tissue in response to the monitored state of the tissue, and (b) monitoring the state of the tissue following (a).

In an embodiment, the apparatus includes a robotic system configured to move the housing in response to a parameter of the monitored state of the tissue.

In an embodiment, the plurality of transducers are not configured to apply a treatment to the tissue in response to the monitored state of the tissue.

In an embodiment, the plurality of transducers are configured to apply a treatment to the tissue in response to the monitored state of the tissue.

In an embodiment, the transmitted energy has a first energy level associated therewith, and, in applying the treatment, the transducers are configured to transmit energy at a second energy level that is higher than the first energy level.

In an embodiment, in monitoring the state of the tissue, the apparatus identifies a concentration of fat in the tissue.

In an embodiment, the apparatus is configured to drive the plurality of transducers to direct energy towards the concentration of fat.

The present invention will be more fully understood from the following detailed description of embodiments thereof, taken together with the drawings, in which:

DETAILED DESCRIPTION OF EMBODIMENTS OF THE INVENTION

Figure 1:
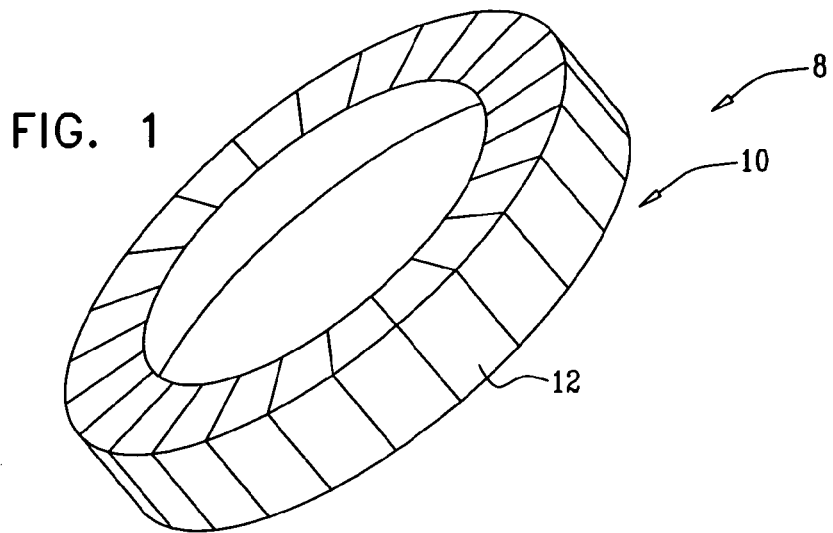
FIG. 1 is a schematic illustration of an ultrasound device in accordance with an embodiment of the present invention.

FIG. 1 is a schematic illustration of an ultrasound device 8, in accordance with an embodiment of the present invention. Ultrasound device 8 comprises a plurality of ultrasound transducers 12, coupled to a support structure. The support structure maintains the transducers in a desired relationship with respect to each other, such as in a ring 10 of ultrasound transducers 12 (as shown), in another closed configuration (e.g., an ellipse), or in an open configuration (e.g., a C-shaped configuration, not shown). For some applications, the support structure comprises a rigid material, to rigidly maintain the desired relationship of the ultrasound transducers with respect to each other. For other applications, the support structure is at least somewhat flexible, to enable the ultrasound transducers to maintain suitable acoustic coupling with rounded tissue of a subject (such as a limb).

Figure 2:
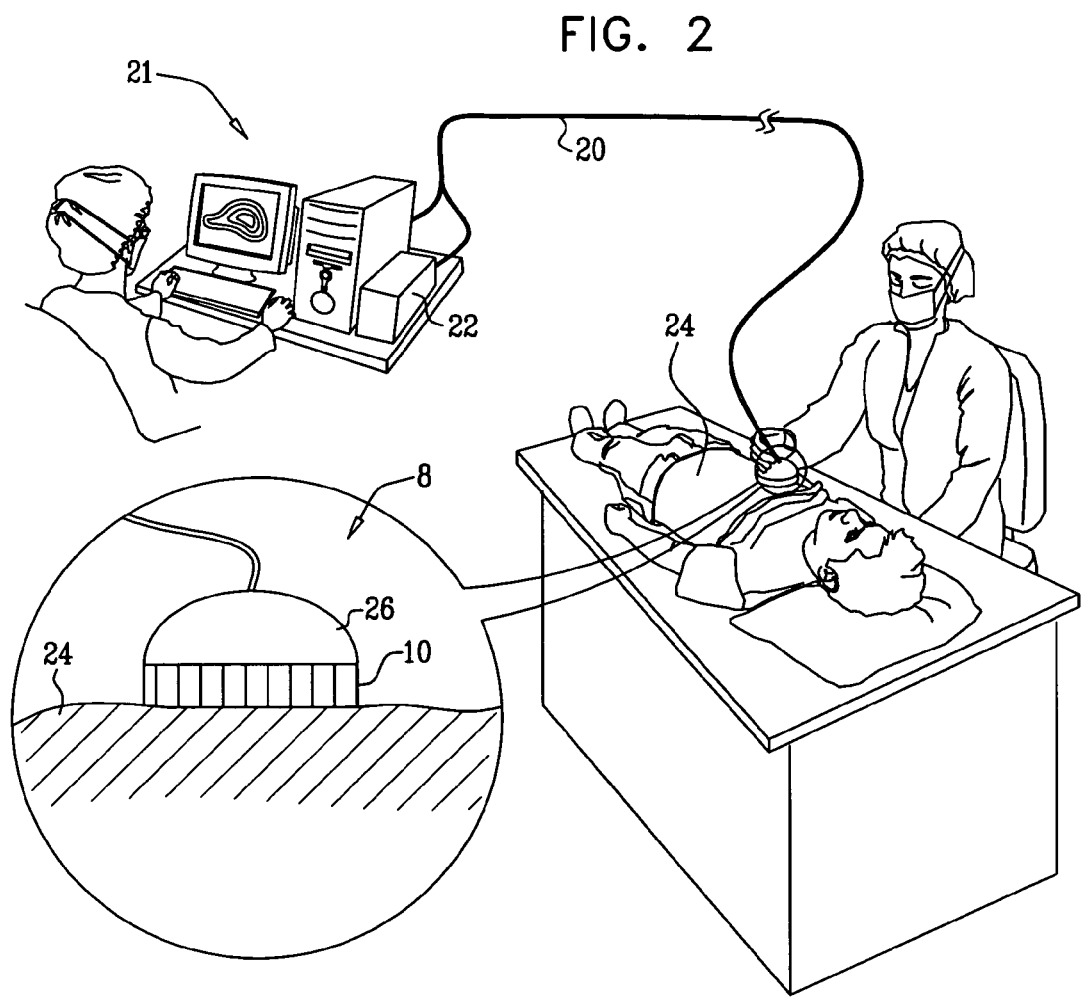
FIG. 2 is a schematic illustration of apparatus comprising the ultrasound device of FIG. 1, positioned on tissue of a subject, in accordance with an embodiment of the present invention.

FIG. 2 is a schematic illustration of ultrasound device 8, coupled to a cover 26, and positioned on tissue 24 of a subject, in accordance with an embodiment of the present invention. Ultrasound transducers 12 of ring 10 are typically connected via coupling lines 20 to a workstation 21 which is configured to drive and receive data from ultrasound transducers 12. Workstation 21 processes signals from transducers 12 in order to generate acoustic maps or images of tissue 24 that is enclosed within ring 10. The resultant maps or images indicate whether a desired extent of treatment has been obtained (e.g., a level of damage to tissue), and guide further treatment.

It is noted that although some embodiments of the present invention are described herein with respect to generally closed-loop operation of ultrasound device 8, the scope of the present invention includes the use of ultrasound device 8 only for monitoring the tissue, while, for example, another device (e.g., a prior art ultrasound device) applies a treatment. Similarly, the scope of the present invention includes the use of ultrasound device 8 only for treating the tissue, while, for example, another device (e.g., a prior art ultrasound device) monitors the progress of the treatment. Alternatively, only monitoring is performed, or only treatment is performed.

An electromechanical system 22 is typically connected to cover 26 via coupling lines 20, to generate suction under cover 26. Optionally, electromechanical system 22 dispenses ultrasound gel to enhance acoustic coupling with the tissue. Alternatively or additionally, electro-mechanical system 22 dispenses water for cooling the device or tissue. Further alternatively or additionally, cover 26, an inner portion of ring 10, or another component comprises a reservoir (not shown) of water and/or gel, for dispensing by an operator during a procedure.

Figure 3:
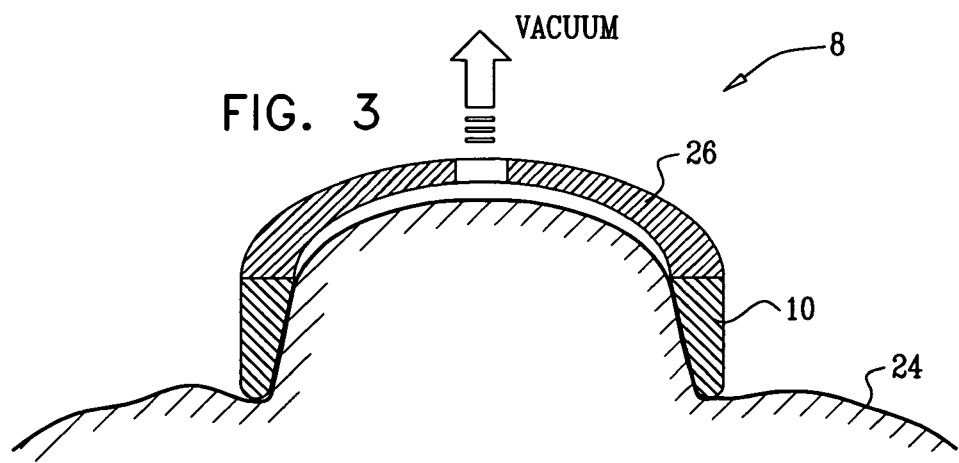
FIG. 3 is a cross-sectional view of a portion of the apparatus shown in FIG. 2, in accordance with an embodiment of the present invention.

Reference is now made to FIGS. 2 and 3. FIG. 3 is a schematic illustration of a portion of ultrasound device 8, in accordance with an embodiment of the present invention. In an embodiment, the operator (as shown) or a robotic system moves ultrasound device 8 to different sites on tissue 24. For example, the tissue may be skin overlying a significant deposit of fat, and the patient may be undergoing a cosmetic procedure to remove the fat. Vacuum is applied by electromechanical system 22 to draw tissue 24 into ring 10. Alternatively, other techniques (such as pinching by hand or by a pinching tool) are used to draw the tissue into ring 10.

Once tissue 24 is firmly secured within ring 10, good acoustic coupling between the tissue and the ring is typically verified, prior to ultrasound device 8 entering a monitoring mode, for example, by transmitting "scout" waves from one side of the ring to the other.

Figure 4:
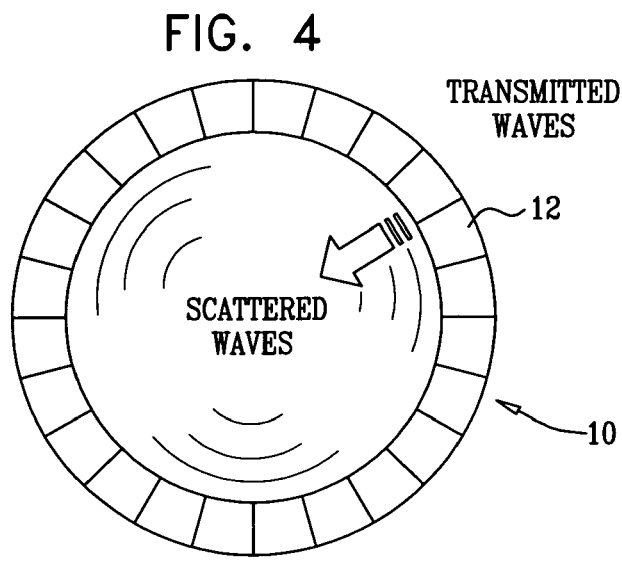
FIG. 4 is a schematic illustration of operation of the apparatus of FIG. 2 in a monitoring mode, in accordance with an embodiment of the present invention.

FIG. 4 is a schematic illustration of operation of ultrasound device 8 in a monitoring mode, in accordance with an embodiment of the present invention. One or more ultrasound transducers 12 transmit low energy waves into tissue 24 enclosed within ring 10. The resulting through-transmitted and/or scattered waves are typically detected by all of the ultrasound transducers (including the one or more transmitting ultrasound transducers), and are recorded for further analysis. The procedure is repeated using different transducers or signal parameters for transmission each time, until a sufficient amount of data is collected.

Maps of acoustic properties or images of the circular tissue area are reconstructed, typically using algorithms that are known in the art. As appropriate, the maps or images may depict various acoustic properties of the tissue, such as reflectivity, speed of sound, attenuation, acoustic impedance, and other properties. For some applications, the maps or images thus acquired are saved for later use as a reference set. In an embodiment, maps of acoustic properties are translated into maps that show tissue type within ring 10, and, for example, differentiate between fat tissue and muscle, nerve or blood cell tissues. Alternatively or additionally, maps of acoustic properties are translated into temperature maps, e.g., using techniques described in the above-cited PCT Publication WO 06/018837 to Azhari et al., which is incorporated herein by reference, and/or using other techniques known in the art. Further alternatively or additionally, maps of acoustic properties are assessed by computer or by a human to determine the efficacy of the treatment, and are saved or used to modify further treatments.

If an external source of energy is used to treat tissue 24 within ring 10, then ultrasound device 8 typically works only in the monitoring mode. Maps or images are typically acquired generally continuously during the treatment. The changes derived from the treatment result in changes of the detected acoustic properties of the treated tissue. By subtracting the new maps or images from the reference set of maps or images, the amount and location of damage is assessed. Alternatively, the reference set is not used, but instead a desired endpoint is designated, and a signal is generated when the endpoint is approached or attained.

In accordance with an embodiment of the present invention, ring 10 is switched to a treatment mode, typically a plurality of times in alternation with the monitoring mode described hereinabove. In the treatment mode, ultrasound transducers 12 transmit high intensity ultrasound waves, shock waves, sharp negative pressure pulses, continuous waves (CW), pulse sequences that cause cavitation, any other form of acoustical radiation that affects the tissue in a desired manner, or any combination of the above. Typically, but not necessarily, the ultrasound transducers transmit the energy in a HIFU mode.

Figure 5:
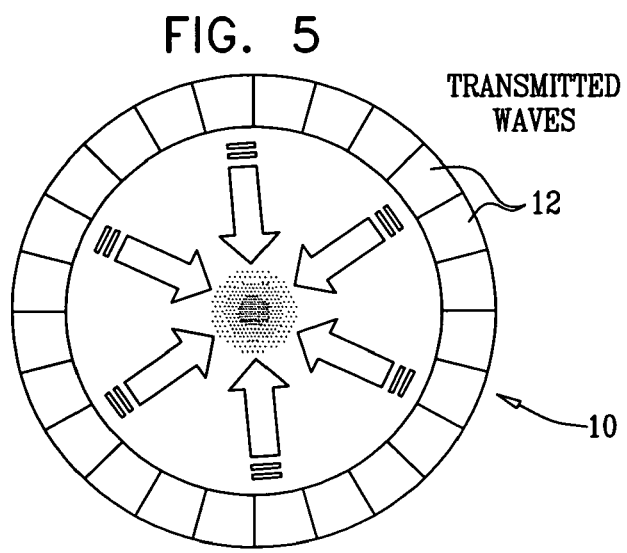
FIG. 5 is a schematic illustration of operation of the apparatus of FIG. 2 in a treatment mode, in accordance with an embodiment of the present invention.

FIG. 5 is a schematic illustration of the operation of ultrasound device 8 in a treatment mode, in accordance with an embodiment of the present invention. During the treatment mode, some or all of ultrasound transducers 12 transmit high intensity waves simultaneously or in a temporal pattern, towards tissue 24 in the center of ring 10. This typically creates an imploding cylindrical wave, whose amplitude (positive or negative) is high at the center. Consequently, damage to the tissue occurs relatively rapidly. Alternatively, other signal protocols create other ultrasound-based effects besides an imploding cylindrical wave, which, nevertheless, produce a desired level of tissue damage. In any case, following the transmission of the energy from transducers 12, ring 10 is typically switched back to the monitoring mode and damage assessment is performed. If appropriate, another iteration of high energy transmission is performed, followed by another iteration of monitoring. The procedure is repeated until satisfactory results are obtained. At this point, the vacuum is released under cover 26 and the operator or the robotic system moves the device to a new region to be treated, optionally based on feedback from the monitoring. It is noted that by using phased array techniques, the phase of the transmitted waves from each ultrasound transducer 12 can be controlled such that the focal point of the imploding wave is moved over a significant portion of the area within ring 10, without physically moving the device.

In some embodiments, a plurality of rings 10 are utilized in order to attain desired results.

For some applications, techniques described herein are practiced in combination with techniques described in one or more of the references cited in the Cross-references section or Background section of the present patent application, which are incorporated herein by reference.

Embodiments of the present invention described herein may be used, for example, for cosmetic purposes, such as by placing ultrasound device 8 in contact with skin of the patient and damaging fatty tissue. The scope of the present invention includes application of the techniques described herein to tissue other than skin, as well. For example, ultrasound device 8 may be sized for placement during surgery on an intrabody organ of the subject, such as the heart or an abdominal organ.

It is noted that although some embodiments of the present invention are described with respect to the use of ultrasound, the scope of the present invention includes replacing the ultrasound transducers described herein with transducers of other forms of energy, such as electromagnetic radiation.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus, comprising:
   a housing, adapted for placement on tissue that includes skin of a subject, such that the tissue may be drawn into the housing;
   a plurality of ultrasound transducers, coupled to the housing at respective locations with respect to the housing so as to define a ring of transducers, at least some of which are configured to transmit energy through the skin towards each other, in a plane defined by the housing, at least some of the plurality of ultrasound transducers being configured to receive the energy by through transmission; and
   a processor configured to monitor the tissue in response to the received energy by calculating an indication of speed of sound in the tissue,
   wherein at least some of the plurality of transducers are configured to apply a treatment to the tissue in response to the monitoring of the tissue.

2. The apparatus according to claim 1, comprising a source of suction configured to draw the tissue into the housing, wherein the transducers are coupled to the housing at respective locations with respect to the housing so as to direct the energy into the tissue within the housing.

3. The apparatus according to claim 1, comprising a pinching tool, configured to draw the tissue into the housing by pinching the tissue, wherein the transducers are coupled to the housing at respective locations with respect to the housing so as to direct the energy into the tissue within the housing.

4. The apparatus according to claim 1, wherein the transducers are configured to substantially avoid transmitting energy out of the plane.

5. The apparatus according to claim 1, wherein the housing is flexible, and configured to flex to match a shape of the tissue.

6. The apparatus according to claim 1, wherein the housing is rigid.

7. The apparatus according to claim 1, wherein the apparatus is configured to apply a treatment to the tissue by elevating a temperature of the tissue by less than 10 C.

8. The apparatus according to claim 7, wherein the apparatus is configured to elevate the temperature by less than 5 C.

9. The apparatus according to claim 1, wherein the processor is configured to monitor a state of the tissue in response to the received energy.

10. The apparatus according to claim 9, wherein the at least some of the plurality of transducers are configured to apply the treatment to the tissue in response to the monitored state of the tissue.

11. The apparatus according to claim 1, further comprising a controller, configured to cause the plurality of transducers to cycle repeatedly between (a) applying a treatment to the tissue in response to the monitoring of the tissue, and (b) monitoring the tissue following (a).

12. The apparatus according to claim 1, comprising a robotic system configured to move the housing in response to a parameter of the monitored tissue.

13. The apparatus according to claim 1, wherein the at least some of the plurality of ultrasound transducers that are configured to transmit the energy through the skin that is received and that is monitored by the processor are configured to configure the energy to have a first energy level associated therewith, and wherein, in applying the treatment, the transducers that apply the treatment are configured to apply the treatment using energy at a second energy level that is higher than the first energy level.

14. The apparatus according to claim 1, wherein in monitoring the tissue, the apparatus identifies a concentration of fat in the tissue.

15. The apparatus according to claim 14, wherein the apparatus is configured to drive the plurality of transducers to direct energy towards the concentration of fat.

16. The apparatus according to claim 1, wherein the processor is configured to generate an image of the tissue in response to the monitoring of the tissue.

17. The apparatus according to claim 1, wherein the processor is configured to monitor temperature of the tissue.

18. The apparatus according to claim 17, wherein the processor is configured to generate a temperature map of the tissue in response to the monitoring of the tissue.

19. The apparatus according to claim 17, wherein the processor is configured to modify further treatments of the tissue in response to the monitored temperature.

* * * * *